United States Patent [19]

Bottenbruch et al.

[11] Patent Number: 4,996,373

[45] Date of Patent: Feb. 26, 1991

[54] PROCESS FOR PRODUCING DIHYDROXYDIARYLALKANES

[75] Inventors: Ludwig Bottenbruch, Krefeld; Heinrich Ruppert, Bergisch Gladbach, both of Fed. Rep. of Germany; Neil S. Isaacs, Henley on Thames; Kenneth G. Latham, Blewsbury Berkshire, both of Great Britain

[73] Assignee: Bayer Aktiengesellschaft, Bayerwerk, Fed. Rep. of Germany

[21] Appl. No.: 419,062

[22] Filed: Oct. 10, 1989

[30] Foreign Application Priority Data

Oct. 15, 1988 [DE] Fed. Rep. of Germany ....... 3835204

[51] Int. Cl.$^5$ ...................... C07C 37/20; C07C 39/16
[52] U.S. Cl. .................................. 568/727; 568/722; 568/728
[58] Field of Search ...................... 568/727, 728, 722

[56] References Cited

U.S. PATENT DOCUMENTS

| | | | |
|---|---|---|---|
| 3,394,089 | 7/1968 | McNutt et al. | 568/728 |
| 4,346,247 | 8/1982 | Faler et al. | 568/728 |
| 4,400,555 | 8/1983 | Mendirrata | 568/728 |
| 4,423,252 | 12/1983 | Maki et al. | 568/728 |
| 4,584,416 | 4/1986 | Pressman et al. | 568/728 |
| 4,820,740 | 4/1989 | Li | 568/728 |

FOREIGN PATENT DOCUMENTS 0001863  5/1979  European Pat. Off. ............ 568/728

OTHER PUBLICATIONS

Schnell, Chemistry & Physics of Polycarbonates, Interscience Publishers 964, pp. 82–83.

*Primary Examiner*—Werren B. Lone
*Attorney, Agent, or Firm*—Joseph C. Gil; Aron Preis

[57] ABSTRACT

The invention relates to a process for producing dihydroxydiarylalkanes from carbonyl compounds and phenols under high pressure.

17 Claims, No Drawings

PROCESS FOR PRODUCING DIHYDROXYDIARYLALKANES

The invention relates to a process for producing dihydroxydiarylalkanes from carbonyl compounds and phenols under high pressure.

Dihydroxydiarylalkanes are known. They are generally produced by condensing aromatic hydroxy compounds with aldehydes or ketones. The best known dihydroxydiarylalkane is 4,4'-dihydroxydiphenyl-2,2-propane. It is obtained from phenol and acetone as follows:

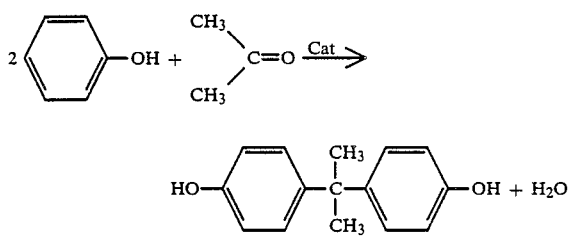

The product is in general shown in short as bisphenol-A (BPA)—the A standing for acetone.

The reaction of phenol and acetone can be catalyzed for example by acids. Strong acids, such as hydrochloric acid, sulphuric acid, sulphonic acid and/or acidic ion exchanger or also aluminum chloride, zinc chloride etc, can therefore be used.

The industrial reaction does not give pure 4,4'-dihydroxyphenyl-2,2-propane, but a mixture, which can contain considerable amounts (up to 20%) of by-products and isomers (eg Ullmann, 4th edition, Vol. 18, p.217 ff).

Phenols and acetones can be reacted together in substance or in inert organic solvents. To obtain pure, marketable bisphenol-A, the primary reaction mixture must be processed. Many stages are necessary for this and also, amongst other things, for eliminating by-products and if necessary catalyst residues (Schnell, Chemistry and Physics of Polycarbonates, Interscience Publishers (964, p. 82/83).

At approximately 30° C., the time taken for the reactants to react fully is approximately 12-24h. The reaction time can be reduced to approximately a third, by increasing the temperature (50° C.-60° C.); despite this, the industrial production of BPA still requires very large reaction vessels. Moreover the proportion of by-products (eg o,-p-isomers) also increases with higher temperatures; at 60° C. it is approximately 7% -10%.

It has now been found, that the reaction of phenols and acetone, if necessary in the presence of catalysts, eg for bisphenol-A, only takes a few minutes at room temperature under pressures of 1000 to 10,000 bar. Thereby pure 4,4'-dihydroxydiphenyl-2,2-propane for example can be obtained in a high yield and with practically no by-products.

The industrial importance of this invention is in the fact that the reaction requires a very low reaction volume, and for example can be carried out in thin tubes. Furthermore the costly separation of by-products and if necessary organic sulphur compounds is avoided.

The process can be carried out with a high degree of success with acetone on other ketones (eg methyl ethyl ketone, cyclohexanone etc) and phenols (eg cresol, eg dimethylphenol).

Object of the invention is therefore a process for producing 4,4'-dihydroxydiphenyl alkanes, preferably 4,4'-dihydroxydiphenyl propane and its derivatives which have been substituted in the aromatic nucleus by $C_1$-$C_3$-alkyl groups, preferably methyl groups or by halogen, preferably Cl, Br, characterized in that an excess of phenols is caused to react with ketones, preferably acetone, at a pressure of at least 1000 bar, optionally in the presence of a catalyst and optionally in the presence of a water-binding agent, at temperatures of 20° C. -100° C.

The following can especially be used for the process: at least 3 moles phenol per 1 mole ketone, preferably acetone. 0-cresol, o-chlorophenyl, 2,6-dimethylphenol, o-ethylphenol, o-isopropylphenol, o-phenylphenol etc, preferably phenol, can be used as the phenol.

Preferably 30 to 3 moles of the phenol per 1 mole ketone, preferably acetone, are used.

The reaction is carried out under high pressure. A pressure of at least 1000 bar is used. The upper pressure limit is only given due to the industrial facilities and in current practice should lie at approximately 10,000 to 15,000 bar. A pressure of approximately 3000 to approximately 6000bar is preferred, and 5000 bar is particularly preferred, because at this pressure optimum results can be achieved with reasonable industrial expenditure. Using high pressures considerably accelerates the reaction (up to a factor of $10^6$), increases the yield and the proportion of 4,4'-dihydroxydiphenyl compounds in the reaction product.

The reaction can be accelerated in a fundamentally known method with basic and acidic catalysts and co-catalysts known for this purpose.

Lewis-acids (such as $ZnCl_2$) proton acids (such as toluene sulphonic acid, chloroacetic acid, water) and hydrogen halides (such as hydrochloric acid, trifluoroacetic acid, boron trifluoride (etherate) etc can be used as the catalyst.

Gaseous catalysts are preferred (eg HCl).

Suitable amounts of catalyst are generally 0.01 to 20 %-by-weight, preferably 1 to 10 %-by-weight, most preferably 4 to 6 %-by-weight, with respect to the phenol.

Ion exchangers containing $SO_3H$-groups or methane sulphonic acid can be used. The catalyst can also contain SH-groups, e.g. ion exchangers containing $SO_3H$-groups, which in turn are coated with mercapto compounds.

Substances holding SH-groups can be used as co-catalysts.

The reaction according to the invention can be carried out with or without solvent. Any organic liquid which is inert according to the reaction conditions, can be used as the solvent, e.g. halogenated hydrocarbons, preferably chlorinated hydrocarbons. By using a solvent as well, the subsequent processing of the reaction mixture is made easier. In general a higher yield is achieved without solvent.

Commercial resins, e.g. sulphonated polystyrene, such as IR 120 (Registered Trade Mark) etc, can be used as ion exchanger resins.

The process according to the invention can be carried out continuously or discontinuously. With the discontinuous method, mixtures of the initial products and if necessary catalysts, water-extracting agents, solvents, are caused to react in a suitable pressure tank under pressure; the reaction product is removed and processed in a known way, e.g. by distillation and/or crystallization. With the continuous method, a tube reactor is used, in which the reactants are continually injected and pass through, and at the end of which they are continuously removed.

if necessary in a solvent. If an excess of phenol is used, non-reacted phenol can be distilled off.

When using an ion exchanger resin as a catalyst, phenol and carbonyl compound, if necessary in a mixture, are guided over the resin under the conditions according to the invention.

| Example | Mole-ratio phenol-ketone | Catalyst %-by-wt | p/kbar | T/°C. | t/min | Yield |
|---|---|---|---|---|---|---|
| 1 | 3:1 | 4% HCl | 5.5 | 25 | 15 | 80 |
| 2 | 3:1 | 4% HCl | 5.5 | 25 | 10 | 83 |
| 3 | 3:1 | 4% HCl | 0.001 | 0–10 | 180 | 30 |
| 4 | 3:1 | 4% HCl | 0.001 | −18 | 3 days | 10 |
| 5 | 3:1 | 4% HCl | 5.5 | 25 | 10 | 75 |
| 6 | 3:1 | 4% HCl | 5.5 | 40 | 10 | 82 |
| 7 | 3:1 | 4% HCl | 5.5 | 60 | 10 | 90 |
| 8 | 3:1 | 4% HCl | 3 | 25 | 10 | 45 |
| 9 | 3:1 | 4% HCl | 5 | 25 | 10 | 71 |
| 10 | 3:1 | 4% HCl | 6.5 | 25 | 10 | 74 |
| 11 | 3:1 | 3.4% HCl | 5 | 25 | 30 | 65 |
| 12 | 4:1 | 2.7% HCl | 5 | 50 | 10 | 90 |
| 13 | 3:1 | 4% tolSO$_3$H | 5 | 25 | 105 | 2 |
| 14 | 3:1 | 4% ClAcOH | 5 | 25 | 105 | 1 |
| 15 | 3:1 | 4% AcOH | 5 | 25 | 105 | 0 |
| 16 | 8:1 | 2.4% HCl | 5 | 25 | 30 | 72 |
| 17 | 8:1 | 2.4% HCl | 5 | 50 | 30 | 91 |
| 18 | 3 1 | 4% TFA | 5 | 25 | 105 | 0 |
| 19 | 3:1 | 4% DABCO | 5 | 25 | 105 | 0 |
| 20 | 3:1 | 4% PhONa | 5 | 25 | 105 | 0 |
| 21 | 3:1 | 4% TFA* | 5 | 25 | 960 | 0 |
| 22 | 3:1 | 4% TFA* | 5 | 25 | 105 | 0 |
| 23 | 3:1 | 4% TFA | 5 | 60 | 30 | 0 |
| 24 | 3:1 | 4% tolSO$_3$H | 5 | 60 | 30 | 15 |
| 25 | 3:1 | 4% aq.TFA | 5 | 60 | 105 | 0 |
| 26 | 3:1 | 4% water | 5 | 60 | 105 | 0 |
| 27A | 3:1 | 5% MSA | 5 | 60 | 30 | 64 |
| 27B | 3:1 | 10% MSA | 5 | 60 | 30 | 80 |
| 27C | 3:1 | 10% MSA | 5 | 60 | 30 | 83 |
| 28 | 3:1 | resin | 5 | 60 | 30 | 95 |
| 29 | 3:1 | 10% MSA | 5 | 60 | 10 | 78 |
| 30 | 3:1 | 4% BF$_3$ | 5 | 60 | 30 | 64 |
| 31 | 3:1 | 12% ZnCl$_2$ | 5 | 60 | 30 | 1 |
| 32 | 3:1 | 1% HCl | 5 | 25 | 10 | 21 |
| 33 | 3:1 | 1% HCl | 5 | 25 | 30 | 23 |
| 34 | 3:1 | 1% HCl | 5 | 60 | 10 | 47 |
| 35 | 3:1 | 1% HCl | 5 | 60 | 30 | 46 |
| 36 | 21.6:1 | 4% MSA | 5 | 60 | 30 | 66 |
| 37 | 21.6:1 | 2% MSA | 5 | 60 | 30 | 54 |
| 38 | 21.6:1 | 4% MSA | 5 | 60 | 15 | 63 |
| 39 | 21.6:1 | 4% MSA | 5 | 60 | 10 | 53 |
| 40 | 21.6:1 | 4% MSA | 5 | 60 | 5 | 53 |
| 41 | 21.6:1 | 4% MSA | 5 | 60 | 1 | 30 |
| 42 | 3:1 | 0.88% HCl | 5 | 60 | 30 | 50 |
| 43 | 3:1 | 0.88% HCl + 0.35% BT | 5 | 60 | 30 | 99 |
| 44 | 3:1 | 2.7% MSA | 5 | 60 | 30 | 25 |
| 45 | 3:1 | 2.7% MSA + 2.0% BT | 5 | 60 | 30 | 78 |
| 46 | 3:1 | 2.7% MSA + trace H$_2$S | 5 | 60 | 30 | 54 |

The process according to the invention produces 4,4'-dihydroxydiphenyl-2,2-propane in large yields and with a high degree of purity. The processing is made easier due to the low proportion of by-products and the reaction times are greatly reduced due to the speed of the reaction and the good yields, thus considerably improving the space/time-yields.

EXAMPLES

The bisphenols are produced in machines which are known for this purpose and also using known production methods.

For example reaction tubes with a length of 1.5 m and inside diameter of 3 cm can be used.

For the reaction, the catalysts used are preferably dosed to the carbonyl compound and phenol separately, HCl : hydrochloric acid
tolSO$_3$H : toluene sulphonic acid
ClAcOH : chloroacetic acid
TFA : trifluoroacetic acid
resin : sulphonated polystyrene
DABCO : triethylene diamine (diazabicyclooctane)
BF$_3$ : boron trifluoride
MSA : methane sulphonic acid
BT : benzyl thiol
H$_2$S : hydrogen sulphide

We claim:

1. A process for producing 4,4'-dihydroxydiphenyl alkanes or its derivatives characterized in that an excess of phenol is caused to react with ketone at a pressure of at least 1000 bar at temperatures of 20 to 100° C.

2. The process of claim 1 characterized in that a catalyst is present in the reaction.

3. Process according to claim 1, characterized in that the pressure is 3000 to 6000 bar and the temperature is 20° C. to 60° C.

4. Process according to claim 2, characterized in that hydrogen chloride or an ion exchanger containing $SO_3H$-groups or methane sulphonic acid is used as the catalyst.

5. Process according to claim 2, characterized in that the catalyst contains SH-groups.

6. In the process for the preparation of 4,4'-dihydroxydiphenyl alkane by reacting excess phenol with a ketone at a temperature of 20 to 100° C., the improvement comprising carrying out the reaction at a pressure of at least 1000 bar.

7. The process of claim 6 wherein said pressure is 1000 to 10,000 bar.

8. The process of claim 6 wherein said alkane is propane.

9. The process of claim 6 wherein said 4,4-dihydroxydiphenyl alkane is substituted in its aromatic nucleus by at least one $C_{1-3}$-alkyl group or by a halogen atom.

10. The process of claim 9 wherein said alkyl is methyl.

11. The process of claim 9 wherein said halogen is Cl or Br.

12. The process of claim 6 wherein said ketone is acetone.

13. The process of claim 6 wherein said reaction is catalyzed.

14. The process of claim 13 wherein said a water-binding agent is present in said reaction.

15. The process of claim 6 wherein said temperature is about 20° C. to 60° C. and said pressure is 3000 to 6000 bar.

16. The process of claim 13 wherein said reaction is catalyzed by hydrogen chloride or by an ion exchanger which contains $SO_3H$-groups or methane sulfonic acid.

17. The process of claim 13 wherein said reaction is catalyzed by a compound containing SH-groups.

* * * * *